(12) United States Patent
Terakado et al.

(10) Patent No.: US 12,295,770 B2
(45) Date of Patent: *May 13, 2025

(54) MEDICAL DISPLAY CONTROL DEVICE, MEDICAL OBSERVATION DEVICE, DISPLAY CONTROL METHOD, AND MEDICAL OBSERVATION SYSTEM

(71) Applicant: Sony Olympus Medical Solutions Inc., Tokyo (JP)

(72) Inventors: Tomoko Terakado, Kanagawa (JP); Keiji Shioda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 147 days.

This patent is subject to a terminal disclaimer.

(21) Appl. No.: 17/897,234

(22) Filed: Aug. 29, 2022

(65) Prior Publication Data

US 2022/0401049 A1 Dec. 22, 2022

Related U.S. Application Data

(63) Continuation of application No. 16/494,772, filed as application No. PCT/JP2017/040116 on Nov. 7, 2017, now Pat. No. 11,478,204.

(30) Foreign Application Priority Data

Mar. 27, 2017 (JP) ................................ 2017-060376

(51) Int. Cl.
*A61B 6/46* (2024.01)
*G06T 7/00* (2017.01)
(Continued)

(52) U.S. Cl.
CPC ............ *A61B 6/463* (2013.01); *G06T 7/0016* (2013.01); *G16H 30/20* (2018.01); *G16H 40/63* (2018.01)

(58) Field of Classification Search
CPC ... A61B 1/0005; A61B 1/00186; A61B 1/043; A61B 1/046; A61B 1/0638; A61B 10/00;
(Continued)

(56) References Cited

U.S. PATENT DOCUMENTS

| | | | |
|---|---|---|---|
| 7,811,229 | B2 | 10/2010 | Sugimoto |
| 2004/0070822 | A1 | 4/2004 | Shioda et al. |

(Continued)

FOREIGN PATENT DOCUMENTS

| | | |
|---|---|---|
| JP | 2006-180926 A | 7/2006 |
| JP | 2010-213995 A | 9/2010 |

(Continued)

OTHER PUBLICATIONS

Supplementary European Search Report issued Feb. 6, 2020 in European Patent Application No. 17902959.0, 7 pages.

(Continued)

*Primary Examiner* — Manuchehr Rahmjoo
(74) *Attorney, Agent, or Firm* — XSENSUS LLP

(57) ABSTRACT

Provided is a medical display control device including a display control unit that causes a first captured medical image and a second captured medical image to be simultaneously displayed, the first captured medical image having been captured in an imaging device in a first imaging mode where imaging is performed with special light, the second captured medical image having been captured in the imaging device in a second imaging mode different from the first imaging mode before the first captured medical image.

19 Claims, 8 Drawing Sheets

(51) Int. Cl.
*G16H 30/20* (2018.01)
*G16H 40/63* (2018.01)

(58) Field of Classification Search
CPC ........ A61B 2090/373; A61B 2090/508; A61B 34/25; A61B 6/463; A61B 90/20; A61B 90/30; A61B 90/361; A61B 90/37; G06T 7/0016; G16H 30/20; G16H 40/63
See application file for complete search history.

(56) References Cited

U.S. PATENT DOCUMENTS

| | | |
|---|---|---|
| 2009/0192390 A1 | 7/2009 | Berguer et al. |
| 2015/0182106 A1 | 7/2015 | King |
| 2017/0211932 A1* | 7/2017 | Zadravec ............. G02B 27/646 |
| 2020/0082789 A1* | 3/2020 | Liu ...................... G09G 3/3648 |

FOREIGN PATENT DOCUMENTS

| | | |
|---|---|---|
| JP | 2011-27895 A | 2/2011 |
| JP | 2017-29471 A | 2/2017 |
| WO | 2015/092882 A1 | 6/2015 |

OTHER PUBLICATIONS

International Search Report and Written Opinion mailed on Feb. 13, 2018 for PCT/JP2017/040116 filed on Nov. 7, 2017, 9 pages.

* cited by examiner

MEDICAL DISPLAY CONTROL DEVICE, MEDICAL OBSERVATION DEVICE, DISPLAY CONTROL METHOD, AND MEDICAL OBSERVATION SYSTEM

CROSS-REFERENCE TO RELATED APPLICATIONS

The present application is a continuation of U.S. application Ser. No. 16/494,772, filed Sep. 17, 2019, which is based on PCT filing PCT/JP2017/040116, filed Nov. 7, 2017 which claims priority to JP 2017-060376, filed Mar. 27, 2017, the entire contents of each are incorporated herein by reference.

TECHNICAL FIELD

The present disclosure relates to a medical display control device, a medical observation device, a display control method, and a medical observation system.

BACKGROUND ART

In recent medical practice, a medical observation device enabling magnified observation of an observation target, such as a lesion, may be used for support of a surgical operation. The medical observation device may be, for example, a medical observation device including an optical microscope, or a medical observation device including an imaging device that functions as an electronic imaging microscope. Hereinafter, the medical observation device including the optical microscope will be referred to as the "optical medical observation device". Furthermore, hereinafter, the medical observation device including the imaging device may be referred to as the "electronic imaging medical observation device", or simply as the "medical observation device".

A technique related to optical medical observation devices has thus been developed, the technique enabling two types of images of different wavelength bands to be captured. A technique described in Patent Literature 1 cited below, for example, is a technique related to a surgical microscope enabling acquisition of a visible light image of a visible wavelength band and a fluorescent image of a near infra-red wavelength band.

CITATION LIST

Patent Literature

Patent Literature 1: Japanese Unexamined Patent Application, Publication No. 2010-213995

DISCLOSURE OF INVENTION

Technical Problem

For example, a surgical microscope (corresponding to an optical medical observation device) described in Patent Literature 1 includes a charge coupled device (CCD) that captures an observation image of light of a visible wavelength band and a CCD that captures an observation image of light of a visible wavelength band, and thereby captures a visible light image of the visible wavelength band and a fluorescent image of the near infra-red wavelength band. Thus, when the technique described in Patent Literature 1 is used, a user who uses the surgical microscope is able to observe two types of images of different wavelength bands.

However, the surgical microscope that uses the technique described in Patent Literature 1, for examples, needs to include two CCDs, which are the CCD that captures the observation image of the light of the visible wavelength band and the CCD that captures the observation image of the light of the visible wavelength band. Use of a configuration including two CCDs like the surgical microscope that uses the technique described in Patent Literature 1 may increase the cost of the device and makes downsizing of the device difficult.

The present disclosure proposes a medical display control device, a medical observation device, a display control method, and a medical observation system, which are novel and improved, and enable captured medical images to be simultaneously displayed on a display screen, the captured medical images having been captured by an imaging device in different imaging modes.

Solution to Problem

According to the present disclosure, there is provided a medical display control device including: a display control unit configured to cause a first captured medical image and a second captured medical image to be simultaneously displayed, the first captured medical image having been captured in an imaging device in a first imaging mode where imaging is performed with special light, the second captured medical image having been captured in the imaging device in a second imaging mode different from the first imaging mode before the first captured medical image.

Moreover, according to the present disclosure, there is provided a medical observation device including: an arm formed of plural links connected to one another via joints; an imaging device supported by the arm; and a display control unit is configured to cause a first captured medical image and a second captured medical image to be simultaneously displayed, the first captured medical image having been captured in the imaging device in a first imaging mode where imaging is performed with special light, the second captured medical image having been captured in the imaging device in a second imaging mode different from the first imaging mode before the first captured medical image.

Moreover, according to the present disclosure, there is provided a display control method executed by a medical display control device, the display control method including: a step of simultaneously displaying a first captured medical image captured in an imaging device in a first imaging mode where imaging is performed with special light, and a second captured medical image captured in the imaging device in a second imaging mode different from the first imaging mode before the first captured medical image.

Moreover, according to the present disclosure, there is provided a medical observation system including: a medical observation device including: an arm formed of plural links connected to one another via joints; and an imaging device supported by the arm; a display device; and a medical display control device including a display control unit is configured to cause a first captured medical image and a second captured medical image to be simultaneously displayed on a display screen of the display device, the first captured medical image having been captured in the imaging device in a first imaging mode where imaging is performed with special light, the second captured medical image having been captured in the imaging device in a second imaging mode different from the first imaging mode before the first captured medical image.

Advantageous Effects of Invention

According to the present disclosure, captured medical images that have been captured by an imaging device in different imaging modes are able to be simultaneously displayed on a display screen.

This effect is not necessarily limiting, and additionally to this effect, or instead of this effect, any effect described in this specification, or any other effect perceivable from this specification may be achieved.

BEST MODE FOR CARRYING OUT THE INVENTION

Hereinafter, a preferred embodiment of the present disclosure will be described in detail, while reference is made to the appended drawings. Redundant explanation of any components having substantially the same functional configuration will be omitted by assignment of the same reference sign to these components, throughout the specification and drawings.

Furthermore, the description will be made below in the following order.
1. Medical Observation System According to Embodiment
2. Display Control Method According to Embodiment
3. Program According to Embodiment Medical Observation System According to Embodiment Described first of all is an example of a medical observation system according to an embodiment.

An example where a medical observation device according to the embodiment is an electronic imaging medical observation device will be described mainly below, but the medical observation device according to the embodiment is not necessarily the electronic imaging medical observation device. For example, the medical observation device according to the embodiment may be "any medical observation device that has plural imaging modes including an imaging mode where imaging is performed with special light (described later) and is able to perform imaging by switching between the imaging modes", such as an endoscope device.

[1] Configuration of Medical Observation System

Figure 1:
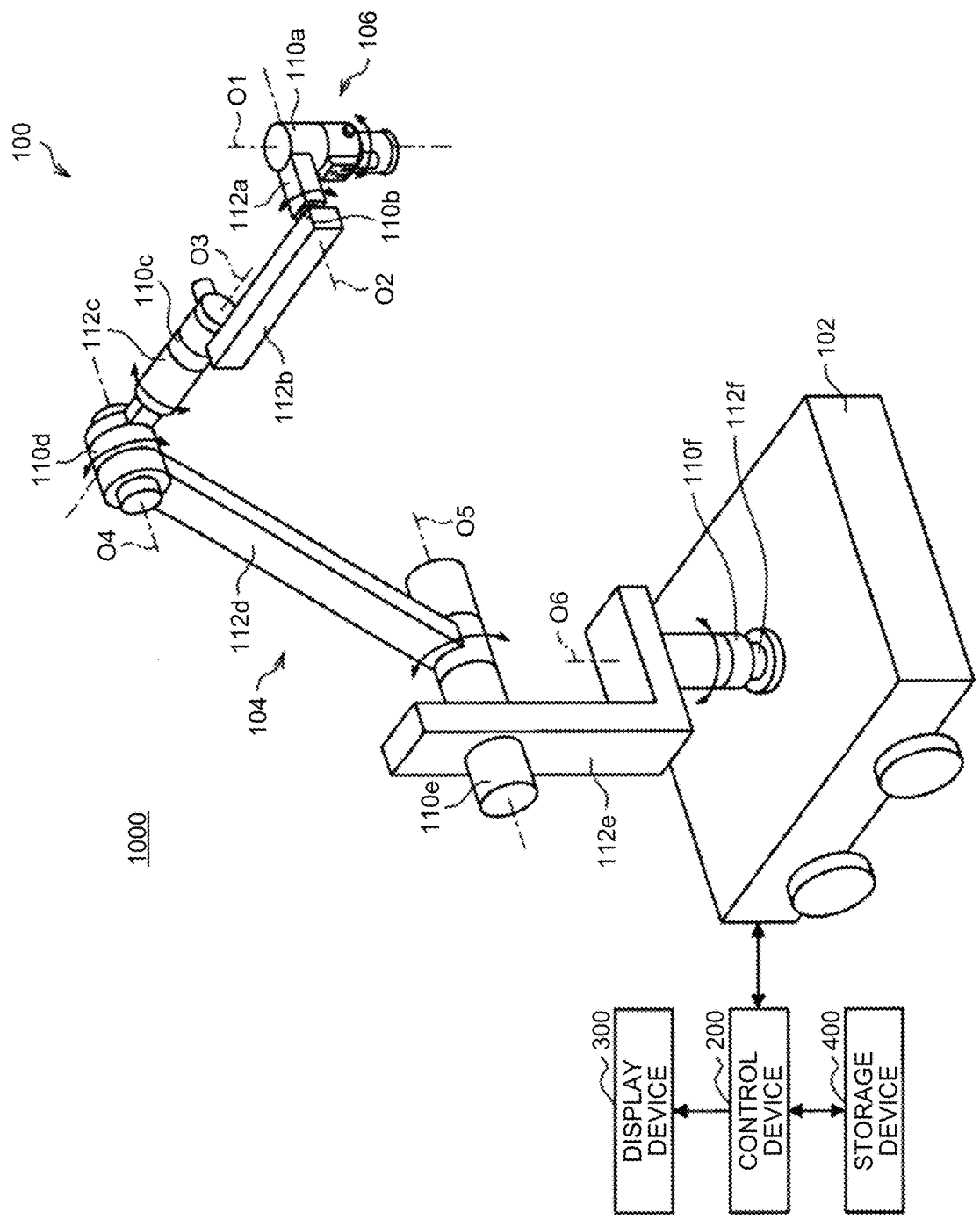
FIG. 1 is an explanatory diagram illustrating a first example of a configuration of a medical observation system according to an embodiment.

FIG. 1 is an explanatory diagram illustrating an example of a configuration of a medical observation system 1000 according to the embodiment. The medical observation system 1000 has, for example, a medical observation device 100, a control device 200, a display device 300, and a storage device 400.

The medical observation system according to the embodiment is not limited to the example illustrated in FIG. 1.

For example, in the medical observation system according to the embodiment, the medical observation device 100 may have functions of the control device 200. If the medical observation device 100 has the functions of the control device 200, the medical observation system according to the embodiment may be, for example, without the control device 200.

Furthermore, in this medical observation system according to the embodiment, for example, the medical observation device 100 or the control device 200 may have functions of the storage device 400. If the medical observation device 100 or the control device 200 has the functions of the storage device 400, the medical observation system according to the embodiment may be, for example, without the storage device 400.

Furthermore, the medical observation system according to the embodiment may be configured to have one or more of: plural medical observation devices 100; plural control devices 200; and plural display devices 300.

If the medical observation system according to the embodiment has plural medical observation devices 100 and plural control devices 200, the medical observation devices 100 and the control devices 200 may be associated with each other one to one, or plural ones of the medical observation devices 100 may be associated with one of the control devices 200. If plural ones of the medical observation devices 100 are associated with one of the control devices 200, at the control device 200, which one of these medical observation devices 100 is to be controlled by that control device 200 is changed by, for example, a switching manipulation being performed.

Furthermore, if the medical observation system according to the embodiment has plural medical observation devices 100 and plural display devices 300, the medical observation devices 100 and the display devices 300 may be associated with each other one to one, or plural ones of the medical observation devices 100 may be associated with one of the display devices 300. If plural ones of the medical observation devices 100 are associated with one of the display devices 300, a captured image captured in which one of these medical observation devices 100 is to be displayed by the display device 300 on a display screen thereof is changed by, for example, a switching manipulation being performed.

Furthermore, as described above, instead of the medical observation device 100 illustrated in FIG. 1, the medical observation system according to the embodiment may have "any medical observation device that has plural imaging modes including an imaging mode where imaging is performed with special light (described later) and is able to perform imaging by switching between the imaging modes".

Figure 2:
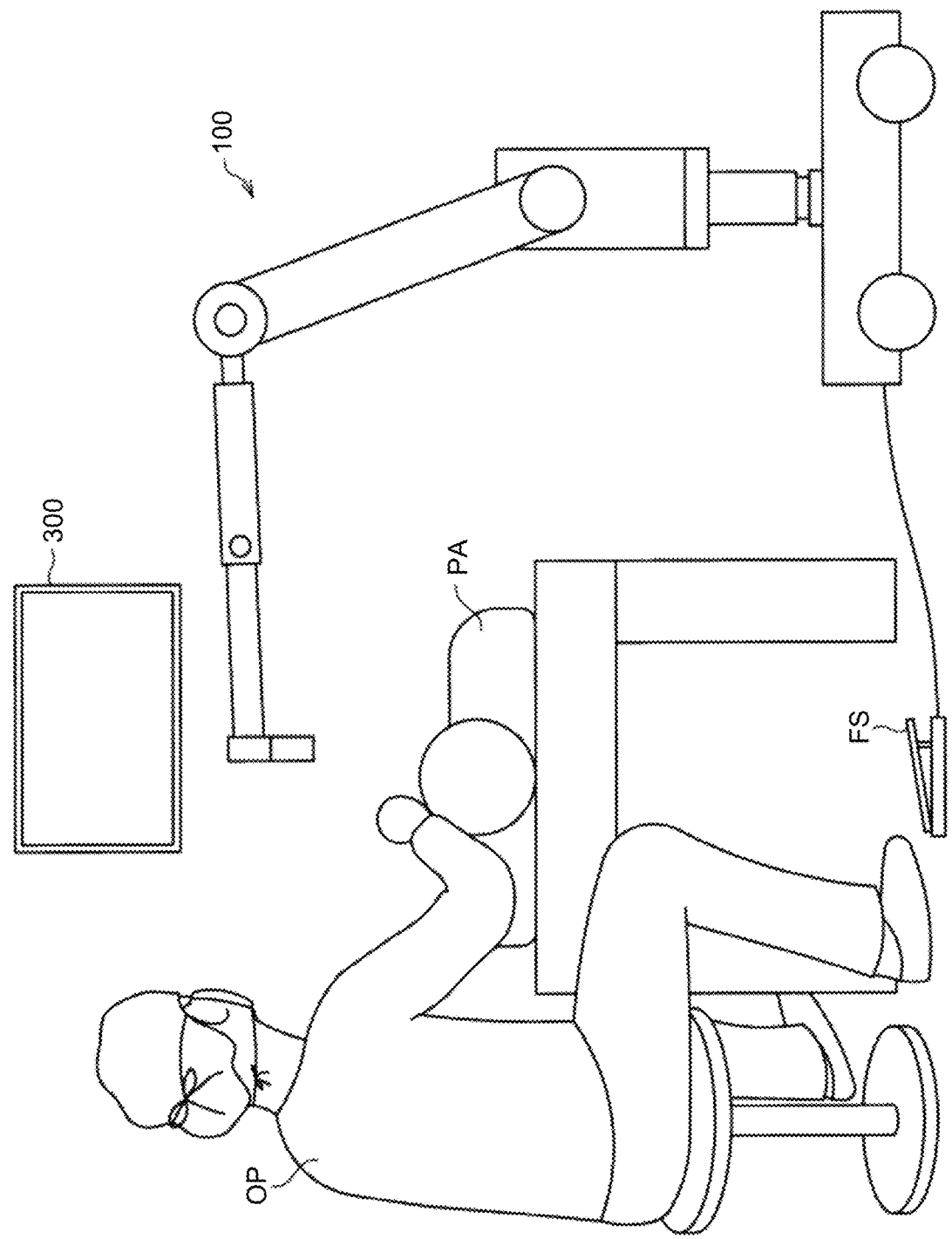
FIG. 2 is an explanatory diagram illustrating an example of a use case where the medical observation system according to the embodiment is used.

FIG. 2 is an explanatory diagram illustrating an example of a use case where the medical observation system 1000 according to the embodiment is used.

An image of a patient PA to be observed (a patient who is a target receiving medical intervention) is captured by an imaging device (described later) included in the medical observation device 100. Hereinafter, a captured image captured by the medical observation device according to the embodiment, such as a captured image having the patient captured therein, is referred to as a "captured medical image", the patient being the target receiving the medical intervention.

A captured medical image captured in the medical observation device 100 is displayed on the display screen of the display device 300. A surgical operator (OP) who administers medical intervention (an example of a user of the medical observation device 100) by using the medical observation device 100 administers medical intervention to the patient PA while looking at the captured medical image being displayed on the display screen of the display device 300.

Furthermore, the surgical operator OP causes an arm (described later), the imaging device (described later), or the like, which is included in the medical observation device 100, to operate, and the medical observation device 100 to be brought into a desired state, by manipulating a manipulation device, such as a foot switch FS, which is external to the medical observation device 100, or a manipulation device (described later) included in the medical observation device 100.

Each device forming the medical observation system 1000 will be described below.

[1-1] Display Device 300

The display device 300 is a display means in the medical observation system 1000, and corresponds to a display device external to the medical observation device 100. The display device 300 displays, for example, various images, such as a captured medical image (a moving image, or plural still images, the same applying hereinafter) captured in the medical observation device 100, and an image related to a user interface (UI), on the display screen. Furthermore, the display device 300 may be configured to enable 3D display. The display in the display device 300 is controlled by, for example, the control device 200.

In the medical observation system 1000, the display device 300 is installed at any place, such as, for example, a wall surface, a ceiling, or a floor surface, of a surgical operating room, the place being visually recognizable by a person, such as a surgical operator, who is involved in a surgical operation in the surgical operating room. The display device 300 may be, for example, a liquid crystal display, an organic electro-luminescence (EL) display, or a cathode ray tube (CRT) display.

The display device 300 is not limited to the above described example.

For example, the display device 300 may be any wearable device, such as a head-mounted display or an eye-wearable device, which is used by being worn by a surgical operator or the like on his/her body.

The display device 300 is driven by, for example, electric power supplied from an internal power source, such as a battery, which is included in the display device 300, or electric power supplied from an external power source connected to the display device 300.

[1-2] Storage Device 400

The storage device 400 is a storage means in the medical observation system 1000, and corresponds to a recording medium external to the medical observation device 100. The storage device 400 includes, for example, any recording medium, such as: a magnetic recording medium, like a hard disk; or a non-volatile memory, like a flash memory, the recording medium being able to store therein data.

The storage device 400 stores therein, for example, various data, such as data representing images, such as a first captured medical image and a second captured medical image, which will be described later, and data related to a patient.

The storage device 400 is connected to an external device, such as the control device 200, through wired communication of any communication scheme or wireless communication of any communication scheme, and the data stored in the storage device 400 are read by the external device as appropriate. FIG. 1 illustrates an example where the storage device 400 is connected to the control device 200, but the storage device 400 may be connected to the medical observation device 100 or the display device 300.

The storage device 400 is driven by, for example, electric power supplied from an internal power source, such as a battery, which is included in the storage device 400, or electric power supplied from an external power source connected to the storage device 400.

[1-3] Control Device 200

The control device 200 controls each of operation in the medical observation device 100 and operation in the display device 300. Furthermore, the control device 200 controls, for example, writing of data into the storage device 400, and reading of data from the storage device 400. That is, the control device 200 plays a role of controlling the operation of the various devices forming the medical observation system 1000.

Furthermore, the control device 200 plays a role of, for example, performing processing related to a later described display control method according to the embodiment. The control device 200 that plays the role of performing the processing related to the later described display control method according to the embodiment functions as a medical display control device in the medical observation system 1000.

By the control device 200 performing the processing related to the later described display control method according to the embodiment, an image according to a result of the processing related to the display control method is displayed on the display screen of the display device 300. An example of the image displayed on the display screen of the display device 300 by the processing related to the display control method according to the embodiment will be described later.

The control device 200 includes, for example: one or more processors (not illustrated in the drawings) each formed of an arithmetic operation circuit, such as a micro processing unit (MPU); a read only memory (ROM, not illustrated in the drawings); a random access memory (RAM, not illustrated in the drawings); a recording medium (not illustrated in the drawings); and a communication device (not illustrated in the drawings). The control device 200 is driven by, for example, electric power supplied from an internal power source, such as a battery, which is included in the control device 200, or electric power supplied from an external power source connected to the control device 200.

The processor (not illustrated in the drawings) performs processing related to control of a control target, such as the medical observation device 100. Furthermore, the processor (not illustrated in the drawings) functions as, for example, a display control unit (described later), and proactively performs the processing related to the later described display control method according to the embodiment. The processing related to the display control method according to the embodiment may be performed by a processing circuit that is separately bodied from the processor (not illustrated in the drawings).

The ROM (not illustrated in the drawings) stores therein a program used by the processor (not illustrated in the drawings), and control data, such as arithmetic operation parameters. The RAM (not illustrated in the drawings) temporarily stores therein the program or the like executed by the processor (not illustrated in the drawings).

The recording medium (not illustrated in the drawings) is a storage means included in the control device 200, and stores therein, for example, various data, such as data related to control and various applications.

Furthermore, the recording medium (not illustrated in the drawings) may have, stored therein, image data representing a captured medical image captured by the imaging device (described later) included in the medical observation device 100 (one or both of image data representing the first captured medical image described later and image data representing the second captured medical image described later). If the image data are stored in the recording medium (not illustrated in the drawings), for example, the control device 200 functions as the storage device 400.

The recording medium (not illustrated in the drawings) may be, for example, a magnetic recording medium, such as a hard disk, or a non-volatile memory, such as a flash memory. Furthermore, the recording medium (not illustrated in the drawings) may be attachable to and detachable from the control device 200.

The communication device (not illustrated in the drawings) is a communication means included in the control device 200, and plays a role of performing communication wirelessly or wiredly with an external device, such as the medical observation device 100, the display device 300, or the storage device 400. The communication device (not illustrated in the drawings) may be, for example: an IEEE 802.15.1 port and a transmitting and receiving circuit (wireless communication); an IEEE 802.11 port and a transmitting and receiving circuit (wireless communication); a communication antenna and a radio frequency (RF) circuit (wireless communication); or a local area network (LAN) terminal and a transmitting and receiving circuit (wired communication).

The control device 200 may be, for example, any device, such as "a medical controller" or "a computer, such as a server", which is able to control the operation of the various devices forming the medical observation system according to the embodiment. Furthermore, if the control device 200 functions as the storage device 400, the control device 200 may be, for example, any device, such as a "recorder", which is able to store therein data. Moreover, the control device 200 may be, for example, an integrated circuit (IC) that is able to be incorporated into the above device.

In one example of control in the control device 200, the control device 200 causes, based on, for example, manipulation of the medical observation device 100, the medical observation device 100 to operate in an operation mode (described later) corresponding to the manipulation. Furthermore, the control device 200 controls, based on, for example, manipulation of the medical observation device 100, imaging in the imaging device (described later) included in the medical observation device 100. The control of the imaging according to the embodiment may be, for example, one or both of control of the zoom magnification and control of the focal distance.

Furthermore, if an image signal transmitted from the medical observation device 100 is received, the image signal having been generated by imaging in the imaging device (described later) included in the medical observation device 100, image processing on the image signal is performed by, for example, the processor (not illustrated in the drawings) in the control device 200. The image processing according to the embodiment may be, for example, one or more of various types of processing, such as gamma correction, white balance adjustment, image enlargement or reduction related to the electronic zoom function, or correction among pixels. In the medical observation system according to the embodiment, the image processing according to the embodiment may be performed in the medical observation device 100.

The control device 200 transmits, for example, a display control signal including a display command, and an image signal subjected to the above image processing, to the display device 300. By the transmission of the display control signal and image signal to the display device 300, a captured medical image having an observation target captured therein (for example, a captured medical image having a site of surgical operation captured therein) is displayed on the display screen of the display device 300, the displayed captured medical image having been enlarged or reduced to a desired magnification by one or both of the optical zoom function and electronic zoom function.

The captured medical image to be displayed on the display screen of the display device 300 by the control device 200 is not limited to the above described example. Examples of the captured medical image to be displayed on the display screen of the display device 300 by the control device 200 will be described later.

[1-4] Medical Observation Device 100

The medical observation device 100 is an electronic imaging medical observation device. For example, if the medical observation device 100 is used in a surgical operation, a surgical operator (an example of a user of the medical observation device 100) observes a site of surgical operation while referring to a captured medical image captured by the medical observation device 100 and displayed on the display screen of the display device 300, and performs various treatments, such as maneuvers according to operative surgical procedures, on the site of surgical operation.

The medical observation device 100 includes, for example, a base 102, an arm 104, and an imaging device 106.

Furthermore, the medical observation device 100 may include, for example, a communication device (not illustrated in the drawings) that performs communication according to a communication scheme corresponding to the communication device (not illustrated in the drawings) included in the control device 200, although this is not illustrated in FIG. 1. For example, if the imaging device 106 and the control device 200 are connected to each other wiredly, the medical observation device 100 is able to be configured to not separately include the communication device (not illustrated in the drawings). The medical observation device 100 is driven by, for example, electric power supplied from an internal power source, such as a battery, which is included in the medical observation device 100, or electric power supplied from an external power source connected to the medical observation device 100.

[1-4-1] Base 102

The base 102 is a base of the medical observation device 100, has one end of the arm 104 connected thereto, and supports the arm 104 and the imaging device 106.

Furthermore, the base 102 has, for example, wheels provided therein, and the medical observation device 100 contacts a floor surface via the wheels. By the provision of the wheels, the medical observation device 100 is able to easily move on the floor surface by means of the wheels.

[1-4-2] Arm 104

The arm 104 is formed of plural links connected to one another via joints.

Furthermore, the arm 104 supports the imaging device 106. The imaging device 106 supported by the arm 104 is three-dimensionally movable, and the position and posture of the imaging device 106 that has been moved are retained by the arm 104.

More specifically, the arm 104 is formed of, for example: plural joints 110a, 110b, 110c, 110d, 110e, and 110f; and plural links 112a, 112b, 112c, 112d, 112e and 112f that are rotatably connected to one another via the joints 110a, 110b, 110c, 110d, 110e, and 110f. A rotatable range of each of the joints 110a, 110b, 110c, 110d, 110e, and 110f is arbitrarily set in the design phase and manufacturing phase, such that desired movement of the arm 104 is realized.

That is, in the medical observation device 100 illustrated in FIG. 1, six degrees of freedom are realized with respect to movement of the imaging device 106, by means of six rotation axes (a first axis O1, a second axis O2, a third axis O3, a fourth axis O4, a fifth axis O5, and a sixth axis O6) corresponding to the six joints 110a, 110b, 110c, 110d, 110e, and 110f that form the arm 104. More specifically, in the medical observation device 100 illustrated in FIG. 1, movement of six degrees of freedom, which are three degrees of translational freedom and three degrees of rotational freedom, is realized.

The joint 110a has a substantially columnar shape, and supports the imaging device 106 (an upper end portion of the imaging device 106 in FIG. 1) rotatably about the rotation axis (the first axis O1) parallel to a center axis of the imaging device 106, by means of a distal end portion (a lower end portion in FIG. 1) of the joint 110a. The medical observation device 100 is formed such that the first axis O1 coincides with the optical axis in the imaging device 106. That is, the field of view of a captured medical image captured by the imaging device 106 is changed as if being rotated, by rotation of the imaging device 106 about the first axis O1 illustrated in FIG. 1.

The link 112a is a member that is substantially rod shaped, and supports the joint 110a fixedly. The link 112a is, for example, extended in a direction orthogonal to the first axis O1, and connected to the joint 110b.

The joint 110b has a substantially columnar shape, and supports the link 112a rotatably about the rotation axis (the second axis O2) orthogonal to the first axis O1. Furthermore, the link 112b is connected fixedly to the joint 110b.

The link 112b is a member that is substantially rod shaped, and is extended in a direction orthogonal to the second axis O2. Furthermore, each of the joint 110b and joint 110c is connected to the link 112b.

The joint 110c has a substantially columnar shape, and supports the link 112b rotatably about the rotation axis (the third axis O3) orthogonal to each of the first axis O1 and second axis O2. Furthermore, one end of the link 112c is fixedly connected to the joint 110c.

By rotation of a distal end (an end where the imaging device 106 is provided) of the arm 104 about the second axis O2 and third axis O3, the imaging device 106 is able to be moved such that position of the imaging device 106 is changed in a horizontal plane. That is, in the medical observation device 100, control of rotation about the second axis O2 and third axis O3 enables movement of the field of view of a captured medical image in a plane.

The link 112c is a member, which has one end having a substantially columnar shape, and another end that is substantially rod shaped. Connection to the one end of the link 112c is performed fixedly, such that the center axis of the joint 110c coincides with the center axis of the substantially columnar shape. Furthermore, the joint 110d is connected to the other end of the link 112c.

The joint 110d has a substantially columnar shape, and supports the link 112c rotatably about the rotation axis (the fourth axis O4) orthogonal to the third axis O3. The link 112d is connected fixedly to the joint 110d.

The link 112d is a member that is substantially rod shaped, and is extended orthogonally to the fourth axis O4. One end of the link 112d is fixedly connected to the joint 110d, so as to abut a side surface of the substantially columnar shape of the joint 110d. Furthermore, the joint 110e is connected to the other end of the link 112d (an end opposite to the end connected to the joint 110d).

The joint 110e has a substantially columnar shape, and supports one end of the link 112d rotatably about the rotation axis (the fifth axis O5) parallel to the fourth axis O4. Furthermore, one end of the link 112e is fixedly connected to the joint 110e.

The fourth axis O4 and the fifth axis O5 are rotation axes that allow the imaging device 106 to be moved in a vertical direction. By rotation of the distal end (the end where the imaging device 106 is provided) of the arm 104 about the fourth axis O4 and fifth axis O5, the position of the imaging device 106 in the vertical direction is changed. Thus, by rotation of the distal end (the end where the imaging device 106 is provided) of the arm 104 about the fourth axis O4 and fifth axis O5, the distance between the imaging device 106 and an observation target, such as a site of surgical operation in a patient, is able to be changed.

The link 112e is a member formed of a combination of: a first member substantially having an L-shape with one side thereof extending in a vertical direction and another side thereof extending in a horizontal direction; and a second member, which extends vertically downward from a portion of the first member, the portion extending in the horizontal direction, and which is rod-shaped. The joint 110e is fixedly connected to a portion of the first member of the link 112e, the portion extending in the vertical direction. Furthermore, the joint 110f is connected to the second member of the link 112e.

The joint 110f has a substantially columnar shape, and supports the link 112e rotatably about the rotation axis (the sixth axis O6) parallel to the vertical direction. Furthermore, the link 112f is connected fixedly to the joint 110f.

The link 112f is a member that is substantially rod shaped, and is extended in the vertical direction. The joint 110f is connected to one end of the link 112f. Furthermore, the other end (an end opposite to the end connected to the joint 110*f*) of the link 112*f* is fixedly connected to the base 102.

By the arm 104 having the above described configuration, in the medical observation device 100, six degrees of freedom are realized with respect to movement of the imaging device 106.

The configuration of the arm 104 is not limited to the example described above.

For example, the joints 110*a*, 110*b*, 110*c*, 110*d*, 110*e*, and 110*f* of the arm 104 may respectively be provided with brakes that restrict rotation at the joints 110*a*, 110*b*, 110*c*, 110*d*, 110*e*, and 110*f* respectively. Examples of the brakes according to the embodiment include brakes of any form, such as brakes that are mechanically driven, and electromagnetic brakes that are electrically driven.

Driving of the brakes is controlled by, for example, the control device 200. By the control of the driving of the brakes, in the medical observation device 100, an operation mode of the arm 104 is set. Examples of the operation mode of the arm 104 include a fixed mode and a free mode.

The fixed mode according to the embodiment is an operation mode where, for example, the position and posture of the imaging device 106 are fixed by restriction of rotation about the rotation axes provided in the arm 104 by means of the brakes.

Furthermore, the free mode according to the embodiment is an operation mode where the rotation axes provided in the arm 104 are freely rotatable by the brakes being released. For example, in the free mode, the position and posture of the imaging device 106 are allowed to be adjusted through direct manipulation by a surgical operator. The direct manipulation according to the embodiment means, for example, manipulation where a surgical operator holds the imaging device 106 in his/her hand and directly moves the imaging device 106.

[1-4-3] Imaging Device 106

The imaging device 106 is supported by the arm 104, and captures an image of an observation target, such as, for example, a site of surgical operation in a patient. Imaging in the imaging device 106 is controlled by, for example, the control device 200.

The imaging device 106 has a configuration corresponding to, for example, an electronic imaging microscope.

Figure 3:
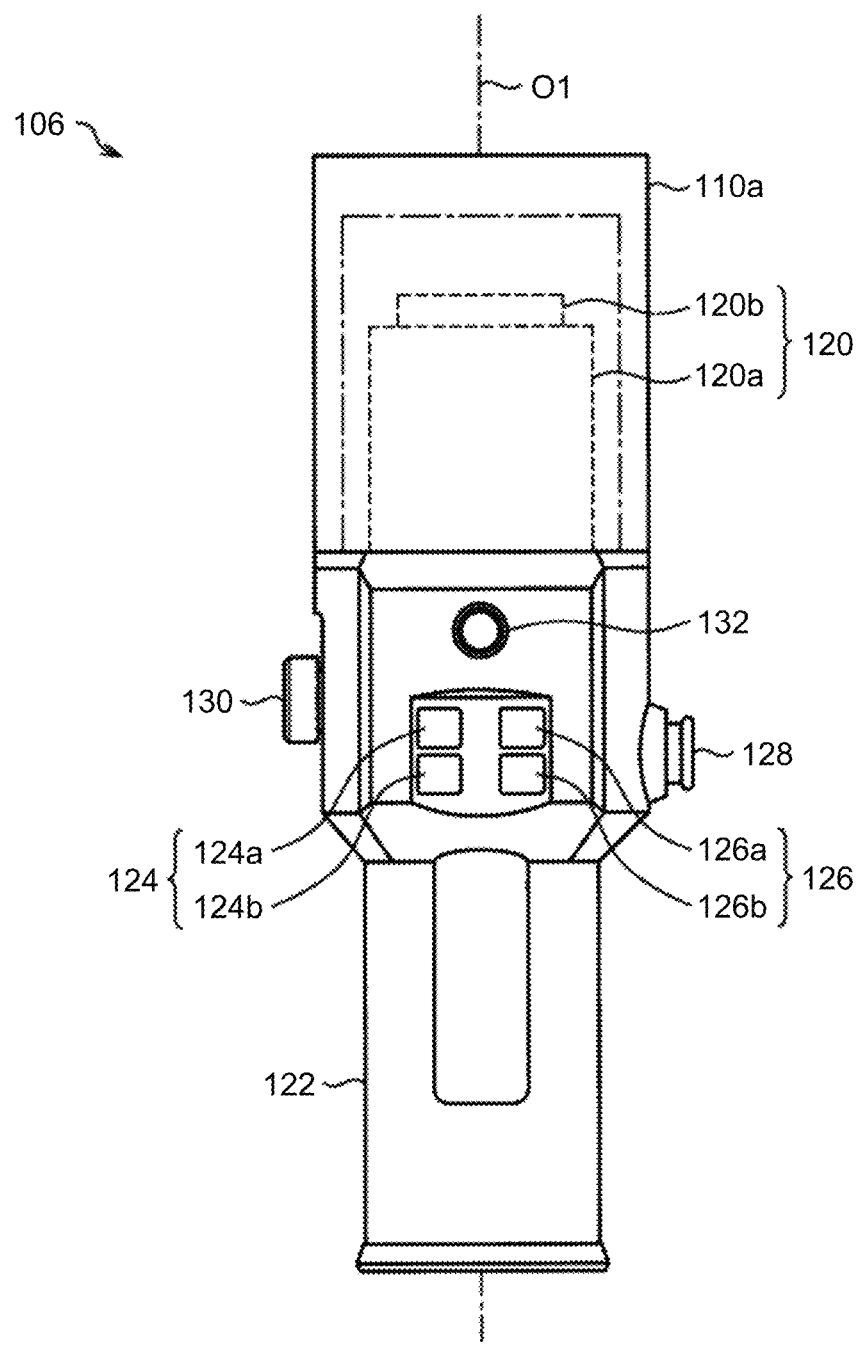
FIG. 3 is an explanatory diagram for explanation of an example of a configuration of an imaging device included in a medical observation device according to the embodiment.

FIG. 3 is an explanatory diagram for explanation of an example of the configuration of the imaging device 106 included in the medical observation device 100 according to the embodiment.

The imaging device 106 has, for example, an imaging member 120, and a cylindrical member 122 having a substantially cylindrical shape, and the imaging member 120 is provided in the cylindrical member 122.

On a plane of an opening at a lower end of the cylindrical member 122 (a lower end in FIG. 3), for example, a cover glass (not illustrated in the drawings) for protecting the imaging member 120 is provided.

Furthermore, for example, a light source (not illustrated in the drawings) is provided inside the cylindrical member 122, and upon imaging, illumination light is emitted from the light source to a subject through the cover glass. Reflected light (observation light) from the subject irradiated with the illumination light enters the imaging member 120 via the cover glass (not illustrated in the drawings), and an image signal representing the subject (an image signal representing a captured medical image) is thereby acquired by the imaging member 120.

Furthermore, a filter that transmits therethrough light of a specific wavelength band and does not transmit therethrough light of other wavelength bands, and a moving mechanism that selectively places the filter onto an optical path are provided inside the cylindrical member 122. The moving mechanism operates in conjunction with, for example, an imaging mode selecting switch (described later), and selectively places the filter onto the optical path correspondingly to a state of the imaging mode selecting switch. The moving mechanism selectively places the filter onto the optical path by moving the filter, based on, for example, a switching signal transmitted according to manipulation of the imaging mode selecting switch (described later).

Examples of the specific wavelength band transmitted through the filter according to the embodiment include: a near infra-red wavelength band (for example, a wavelength band from about 0.7 micrometers to about 2.5 micrometers); a fluorescent wavelength band according to fluorescent observation by use of 5-aminolevulinic acid (5-ALA) (for example, a wavelength band from about 0.6 micrometers to about 0.65 micrometers); and a fluorescent wavelength band of indocyanine green (ICG) (for example, a wavelength band from about 0.82 micrometers to about 0.85 micrometers).

In the medical observation device 100, a filter according to a use where the medical observation device 100 is used is provided in the imaging device 106.

In the medical observation device 100, plural filters where wavelength bands transmitted therethrough are different from one another may be provided in the imaging device 106. If the plural filters are provided in the imaging device 106, the moving mechanism selectively places one of the plural filters onto the optical path, the one corresponding to a state of the imaging mode selecting switch.

By the filter being placed onto the optical path, the imaging device 106 is allowed to perform imaging with light of a specific wavelength band corresponding to the filter.

The above description is on an example where imaging is performed with light of a specific wavelength band by placement of a filter on the optical path, but needless to say, the configuration of medical observation device 100 for performing imaging with light of a specific wavelength band is not limited to the above described example.

Hereinafter, light of a specific wavelength band will be referred to as "special light". Furthermore, hereinafter, light with its wavelength band not limited by a filter or the like will be referred to as "natural light", distinctively from special light.

Any configuration used in various known electronic imaging microscopes is able to be adopted for the imaging member 120.

For example, the imaging member 120 is configured to include, for example: an optical system 120*a*; and an image sensor 120*b* including an imaging element that captures an image of an observation target by means of light that has passed through the optical system 120*a*. The optical system 120*a* is formed of, for example: one or more of lenses, such as an objective lens, a zoom lens, and a focus lens; and an optical element, such as a mirror. The image sensor 120*b* may be, for example, an image sensor having plural imaging elements used therein, the imaging elements being, for example, complementary metal oxide semiconductors (CMOSs) or CCDs.

The imaging member 120 may be configured to have a pair of imaging elements, that is, configured to function as a so-called stereo camera. The imaging member 120 is installed with one or more functions generally included in an electric imaging microscope, such as auto focus functions including at least a zoom function (one or both of an optical zoom function and an electronic zoom function).

Furthermore, the imaging member 120 may be configured to enable imaging of so-called high definition, for example, 4K or 8K. By the imaging member 120 being configured to enable high definition imaging, display of an image by the display device 300 having a large display screen of, for example, 50 inches or more, is enabled with predetermined definition (for example, full HD image quality) ensured, and thus visual recognizability by a surgical operator looking at the display screen is improved. Moreover, by the imaging member 120 being configured to enable high definition imaging, predetermined definition is able to be ensured even if a captured medical image is displayed enlarged by the electronic zoom function on the display screen of the display device 300. In addition, when predetermined definition is ensured by use of the electronic zoom function, performance of the optical zoom function in the imaging device 106 is able to be reduced, and thus the optical system of the imaging device 106 is able to be simplified more, and the imaging device 106 is able to be downsized more.

Furthermore, as described above, the imaging member 120 may be provided with, for example, the above described filter, and a moving mechanism that selectively places the filter onto the optical path.

The imaging device 106 is provided with, for example, various manipulation devices for controlling the operation of the imaging device 106. For example, in FIG. 3, a zoom switch 124, a focus switch 126, an operation mode selecting switch 128, an imaging mode selecting switch 130, and a display changing switch 132 are provided in the imaging device 106. Needless to say, the positions and forms where the zoom switch 124, the focus switch 126, the operation mode selecting switch 128, the imaging mode selecting switch 130, and the display changing switch 132 are provided are not limited to the example illustrated in FIG. 3.

The zoom switch 124 and the focus switch 126 are examples of manipulation devices for adjusting imaging conditions in the imaging device 106.

The zoom switch 124 is formed of, for example, a zoom-in switch 124a that increases the zoom magnification (the magnifying power), and a zoom-out switch 124b that decreases the zoom magnification. By manipulation of the zoom switch 124, the zoom magnification is adjusted and zooming is adjusted.

The focus switch 126 is formed of, for example, a distant view focus switch 126a that increases the focal distance to an observation target (a subject), and a near view focus switch 126b that decreases the focal distance to the observation target. By manipulation of the focus switch 126, the focal distance is adjusted and focusing is adjusted.

The operation mode selecting switch 128 is an example of a manipulation device for selecting an operation mode of the arm 104 in the imaging device 106. By manipulation of the operation mode selecting switch 128, the operation mode of the arm 104 is changed. Examples of the operation mode of the arm 104 include, as described above, the fixed mode and the free mode.

Examples of the manipulation of the operation mode selecting switch 128 include manipulation where the operation mode selecting switch 128 is pressed down. For example, while a surgical operator is holding the operation mode selecting switch 128 down, the operation mode of the arm 104 is in the free mode, and when the surgical operator is not holding the operation mode selecting switch 128 down, the operation mode of the arm 104 is in the fixed mode.

The imaging mode selecting switch 130 is an example of a manipulation device for selecting an imaging mode of the imaging device 106.

Examples of the imaging mode of the imaging device 106 according to the embodiment include: an imaging mode where imaging is performed with special light (hereinafter, referred to as the "first imaging mode"); and one or more imaging modes that are different from the first imaging mode (hereinafter, referred to as the "second imaging mode/modes"). Examples of the second imaging mode according to the embodiment include: an imaging mode where imaging is performed with natural light; and an imaging mode where imaging is performed by use of an image enhancement observation technique, such as narrow band imaging (NBI).

Hereinafter, a captured medical image captured in the first imaging mode may be referred to as a "first captured medical image".

Furthermore, hereinafter, one of captured medical images captured in the second imaging mode, the one having been captured in the second imaging mode before the first captured medical image may be referred to as a "second captured medical image".

The captured medical image captured in the second imaging mode before the first captured medical image means a captured medical image captured before a time point, at which the first captured medical image serving as a reference was captured. The first captured medical image serving as a reference may be, for example, a first captured medical image being displayed on the display screen of the display device 300 (or a first captured medical image that the control device 200 causes to be displayed on the display screen).

The second captured medical image according to the embodiment is specified from captured medical images captured in the second imaging mode by, for example, the processing being performed, the processing being related to the later described display control method according to the embodiment.

Figure 4:
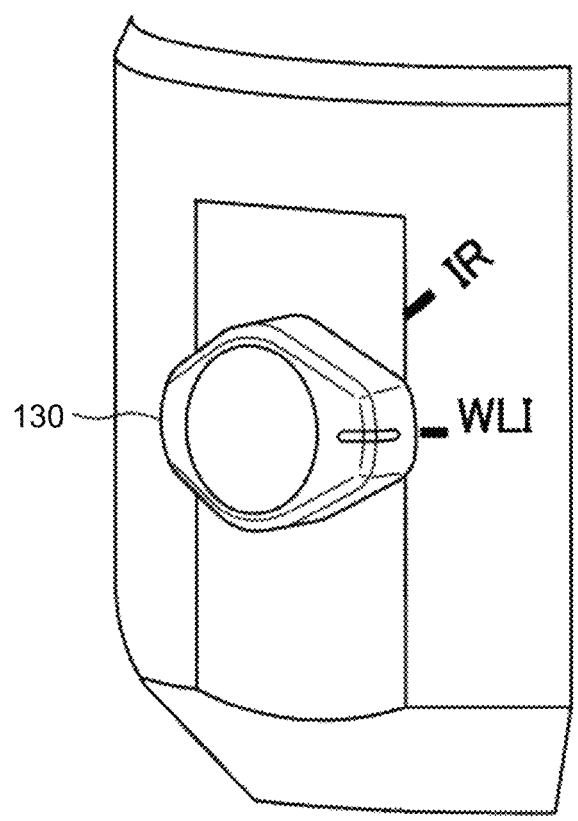
FIG. 4 is an explanatory diagram illustrating an example of an imaging mode selecting switch forming the imaging device included in the medical observation device according to the embodiment.

FIG. 4 is an explanatory diagram illustrating an example of the imaging mode selecting switch 130 that forms the imaging device 106 included in the medical observation device 100 according to the embodiment. FIG. 4 illustrates an example where the imaging mode selecting switch 130 is a rotary switch. Needless to say, the imaging mode selecting switch 130 is not necessarily a rotary switch.

When the imaging mode selecting switch 130 is in a state where "IR" illustrated in FIG. 4 has been selected, the imaging device 106 operates in an imaging mode (an example of the first imaging mode) where imaging is performed with light of a near infra-red wavelength band. When the imaging mode selecting switch 130 is in the state where "IR" illustrated in FIG. 4 has been selected, a "filter that transmits therethrough light of the near infra-red wavelength band and does not transmit therethrough light of the other wavelength bands" is placed onto the optical path in the imaging device 106.

When the imaging mode selecting switch 130 is in a state where "WLI" illustrated in FIG. 4 has been selected, the imaging device 106 operates in an imaging mode (an example of the second imaging mode) where imaging is performed with natural light. When the imaging mode selecting switch 130 is in the state where "WLI" illustrated in FIG. 4 has been selected, the "filter that transmits therethrough light of the near infra-red wavelength band and does not transmit therethrough light of the other wavelength bands" is not placed on the optical path in the imaging device 106.

A surgical operator who uses the medical observation device 100 (an example of a user of the medical observation device 100) manipulates the imaging mode selecting switch 130 and selects "IR" illustrated in FIG. 4 or "WLI" illustrated in FIG. 4, and is thereby able to change the imaging mode.

Hereinafter, a case where the first imaging mode is an imaging mode where imaging is performed with light of a near infra-red wavelength band and the second imaging mode is an imaging mode where imaging is performed with natural light will be described as an example. Furthermore, hereinafter, a state where the medical observation device 100 performs imaging in an imaging mode where imaging is performed with special light, such as light of a near infra-red wavelength band, may be referred to as "special light observation", and a state where imaging is performed with natural light may be referred to as "natural light observation".

The first imaging mode according to the embodiment is not necessarily the imaging mode where imaging is performed with light of a near infra-red wavelength band as described above, and may be a fluorescent wavelength band of fluorescent observation by use of 5-ALA. Furthermore, the medical observation device 100 may enable switch-over among plural first imaging modes.

Furthermore, the second imaging mode according to the embodiment is not necessarily the imaging mode where imaging is performed with natural light as described above, and may be an imaging mode where imaging is performed by use of a specific technique, such as NBI. Moreover, as described above, the number of the second imaging modes according to the embodiment is not necessarily one, and may be two or more.

The example of the configuration of the imaging device 106 will be described by reference to FIG. 3 again. The display changing switch 132 is an example of a manipulation device for changing display on the display screen in the imaging device 106. FIG. 3 illustrates an example where the display changing switch 132 is a button switch. Needless to say, the display changing switch 132 is not necessarily a button switch.

For example, when the display changing switch 132 is in an on-state, plural images are simultaneously displayed on the display screen of the display device 300. The plural images simultaneously displayed on the display screen of the display device 300 may include, for example, the first captured medical image and the second captured medical image. A case where two images are simultaneously displayed on the display screen of the display device 300 when the display changing switch 132 is in the on-state will be described below as an example.

Furthermore, when the display changing switch 132 is in an off-state, a single image is displayed on the display screen of the display device 300. The single image displayed on the display screen of the display device 300 may be, for example, a captured medical image corresponding to a state of the imaging mode selecting switch 130, that is, a captured medical image (a first captured medical image) captured in the first imaging mode or a captured medical image captured in the second imaging mode.

The display changing switch 132 may be referred to as the "simultaneous display button" below.

FIG. 3 illustrates an example where one display changing switch 132 is provided in the imaging device 106, but any number of display changing switches 132 corresponding to display changing patterns that are set may be provided in the imaging device 106.

An image signal generated by imaging in the imaging device 106 is transmitted to, for example, the control device 200, and in the control device 200, various types of image processing are performed on the image signal.

The medical observation device 100 has, for example, the configuration described above by reference to FIG. 1, FIG. 3, and FIG. 4.

The configuration of the medical observation device according to the embodiment is not limited to the configuration described by reference to FIG. 1, FIG. 3, and FIG. 4.

For example, FIG. 1 illustrates an example where the arm 104 is configured to realize six degrees of freedom with respect to driving of the imaging device 106, but the configuration of the arm 104 is not limited to the configuration where the number of degrees of freedom related to the driving of the imaging device 106 is six. For example, the arm 104 may just be configured to be able to move the imaging device 106 as appropriate according to a use, and the number and arrangement of the joints and links, and the directions of the drive axes of the joints are able to be set as appropriate such that the arm 104 has desired freedom.

Furthermore, FIG. 3 illustrate an example where the various manipulation devices for controlling the operation of the imaging device 106 are provided in the imaging device 106, but a part or all of the manipulation devices illustrated in FIG. 3 may be not provided in the imaging device 106. For example, the various manipulation devices for controlling the operation of the imaging device 106 may be provided in another part forming the medical observation device according to the embodiment, the part being other than the imaging device 106. Moreover, in another example, the various manipulation devices for controlling the operation of the imaging device 106 may include an external manipulation device, such as a remote controller or a foot switch.

Furthermore, as described above, the medical observation device according to the embodiment may have functions of the control device 200. If the medical observation device according to the embodiment has functions of the control device 200, the medical observation device includes a processor, such as an MPU, and various types of processing for realizing the functions of the control device 200 are performed in the processor.

Furthermore, as described above, the medical observation device according to the embodiment may have functions of the storage device 400. If the medical observation device according to the embodiment has functions of the storage device 400, the medical observation device includes any recording medium, such as a non-volatile memory, which is able to store therein data.

Display Control Method According to Embodiment

The display control method according to the embodiment will be described next, the display control method being applied to the medical observation system according to the embodiment.

A case where the display control method according to the embodiment is applied to the medical observation system 1000 illustrated in FIG. 1 and the processing related to the display control method according to the embodiment is executed by the control device 200 will be described below as an example. That is, a case where the control device 200 functions as a medical display control device in the medical observation system 1000 illustrated in FIG. 1 will be described below as an example.

If, for example, the medical observation device according to the embodiment has the functions of the control device 200, the processing related to the display control method according to the embodiment is executed by the medical observation device according to the embodiment. That is, in the medical observation system according to the embodiment, the medical observation device according to the embodiment may function as a medical display control device.

[I] Example of Operation of Medical Observation System 1000

An example of operation of the medical observation system 1000 will be described, before explanation of the processing related to the display control method according to the embodiment.

Figure 5:
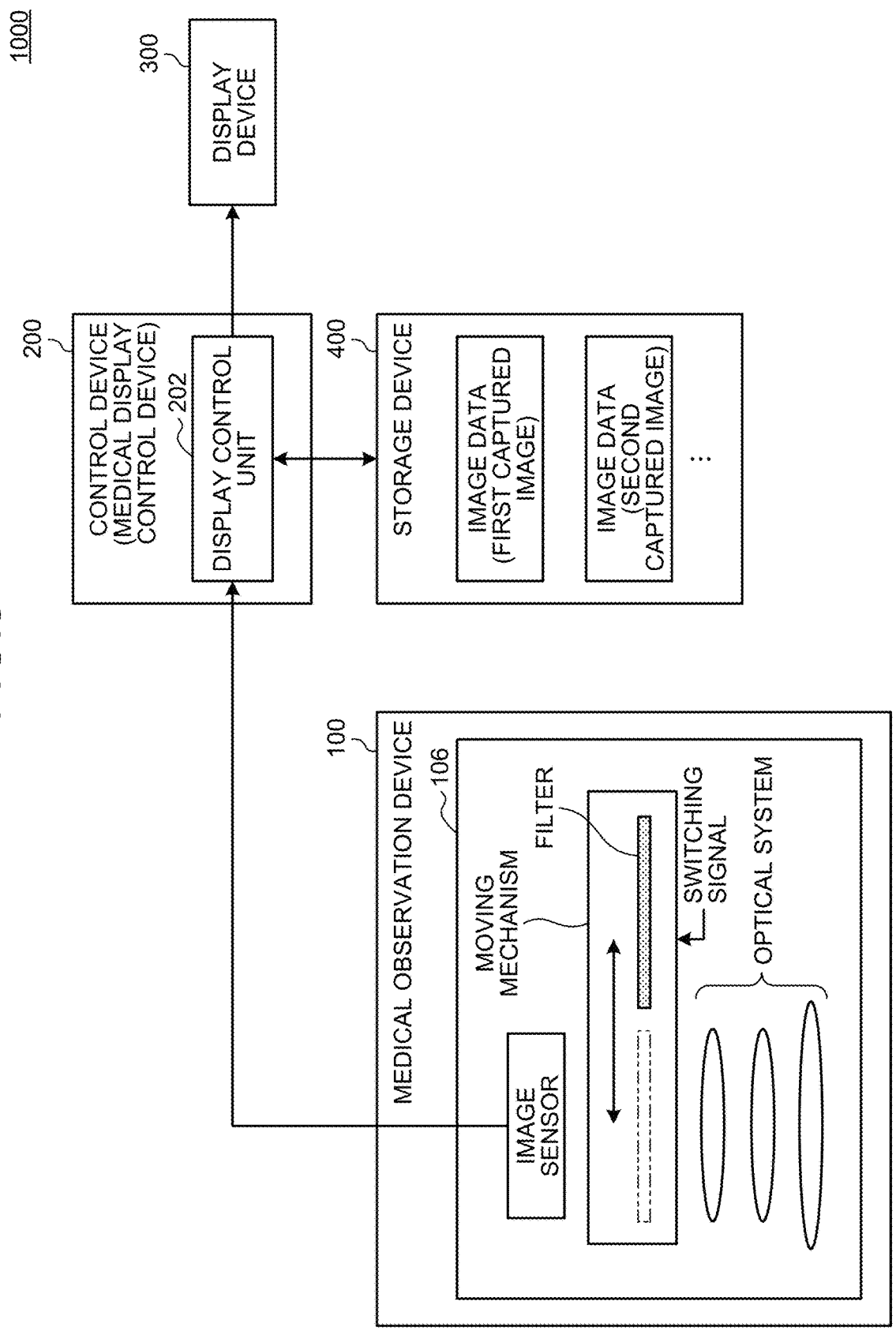
FIG. 5 is block diagram illustrating an example of a configuration of the medical observation system according to the embodiment, to which a display control method according to the embodiment is applied.

FIG. 5 is a block diagram illustrating an example of a configuration of the medical observation system 1000 according to the embodiment, to which the display control method according to the embodiment is applied. FIG. 5 illustrates a part of a configuration of each device forming the medical observation system 1000 described by reference to FIG. 1, the part being related to the display control method according to the embodiment.

An image signal generated by imaging in the imaging device 106 included in the medical observation device 100 is transmitted to the control device 200.

In the control device 200, a display control unit 202 processes the received image signal. Furthermore, the display control unit 202 causes an image to be displayed on the display screen of the display device 300, and stores image data into the storage device 400. In the control device 200, as described above, for example, the processor (not illustrated in the drawings) functions as the display control unit 202.

The display control unit 202 transmits, for example, a display control signal, and an image signal that has been subjected to predetermined image processing as appropriate, to the display device 300. For example, the display control unit 202 transmits, based on a result of the processing related to the later described display control method according to the embodiment, "a display control signal including a display command that causes plural images to be simultaneously displayed on the display screen, and image signals corresponding to the plural images", or "a display control signal including a display command that causes a single image to be displayed on the display screen, and an image signal corresponding to the single image", to the display device 300.

The display device 300 that has received the display control signal and the image signal/signals displays, for example, an image or images represented by the image signal/signals on the display screen, according to the display control signal.

Furthermore, the display control unit 202 transmits a recording control signal including a recording command, and image data representing an image that has been subjected to predetermined image processing as appropriate, to the storage device 400. The storage device 400 that has received the recording control signal and image data stores the image data, according to the recording control signal.

The display control unit 202 changes the format of the image to be stored in the storage device 400, for example, according to the imaging mode in the imaging device 106 included in the medical observation device 100.

For example, if the imaging device 106 included in the medical observation device 100 is operating in the imaging mode where imaging is performed with natural light (an example of the second imaging mode), the display control unit 202 stores, as still images, images represented by image signals that have been received, into the storage device 400, at predetermined time intervals. The predetermined time interval may be, for example, a fixed time interval, such as one second, or a variable time interval that is variable based on manipulation by a person, such as a medical worker, who uses the medical observation system 1000.

If still images corresponding to the second imaging mode are stored in the storage device 400 at predetermined time intervals, the display control unit 202 may compare the number of sets of image data representing still images stored in the storage device 400 with a predetermined threshold that has been set, and cause overwriting and updating according to a result of the comparison, in order from a still image that has been stored in the storage device 400 for a longer time period (that is, an old still image). If, for example, the number of sets of image data representing the still images exceeds the predetermined threshold (or the number of sets of image data representing the still images becomes equal to or greater than the predetermined threshold), the display control unit 202 causes the overwriting and updating. The predetermined threshold may be a fixed value, or may be a variable value that is variable based on manipulation by a person who uses the medical observation system 1000.

For example, by overwriting and updating of still images stored in the storage device 400 as described above, the total data size of captured medical images captured in the second imaging mode and stored in the storage device 400 is able to be limited.

Furthermore, in another example, if the imaging device 106 included in the medical observation device 100 is operating in the imaging mode where imaging is performed with light of a near infra-red wavelength band (an example of the first imaging mode), the display control unit 202 stores, as a moving image, an image represented by an image signal that have been received, into the storage device 400. The display control unit 202 stores, as a single moving image, for example, "after the imaging mode is switched to the imaging mode where imaging is performed with light of the near infra-red wavelength band from the other imaging mode, until the imaging mode where imaging is performed with light of the near infra-red wavelength band is changed to the other imaging mode", into the storage device 400. A moving image corresponding to the first imaging mode as described above is used, for example, as a moving image for automatic play-back.

Needless to say, the display control unit 202 is able to store images of the same format into the storage device 400 regardless of the imaging mode in the imaging device 106 included in the medical observation device 100.

In the medical observation system 1000, by the operation of each device as described above, for example, a captured medical image captured in the medical observation device 100 is displayed on the display screen of the display device 300, and image data representing the captured medical image are stored in the storage device 400.

[II] Example of Processing Related to Display Control Method According to Embodiment The processing related to the display control method according to the embodiment will be described next. In the following description, it will be assumed that the processing related to the display control method according to the embodiment is performed by the control device 200. As described above, in the control device 200, the processing related to the display control method according to the embodiment is performed by, for example, the processor (not illustrated in the drawings) serving as the display control unit 202.

The control device 200 controls display of captured medical images.

For example, the control device 200 causes a first captured medical image and a second captured medical image to be displayed simultaneously. The second captured medical image to be displayed on the display screen simultaneously with the first captured medical image may be, for example, a still image. The second captured medical image to be simultaneously displayed with the first captured medical image may be a moving image.

The first captured medical image and the second captured medical image are captured medical images that have been captured in different imaging modes in a single imaging device, such as the imaging device 106 included in the medical observation device 100. Therefore, by the control device 200 performing the processing related to the display control method according to the embodiment, in the medical observation system 1000, simultaneous display of captured medical images on a display screen is realized, the captured medical images having been captured in an imaging device in different imaging modes.

Furthermore, since the second captured medical image is an image captured before the first captured medical image, the imaging device does not need to have a configuration for acquiring captured images captured simultaneously in plural imaging modes. Therefore, when the display control method according to the embodiment is used, the imaging device does not need to have a configuration including two CCDs like a surgical microscope that uses the technique described in Patent Literature 1, and thus increase in cost of the imaging device is able to be prevented and downsizing of the imaging device is facilitated.

As described with respect to a later described example of operation of the medical observation system, the control device 200 is also able to display, for example, one of the first captured medical image and the second captured medical image.

More specifically, the control device 200 controls display of captured medical images by performing a part or all of, for example: control related to a first example described in Section (1) below to control related a fourth example described in Section (4) below. The control described in Sections (1) to (4) below is realized by, for example, the control device 200 transmitting a display control signal and an image signal to a device for display of an image, such as the display device 300, as described above.

(1) First Example of Control Related to Display Control Method: Control Related to How Captured Medical Images are Displayed Control related to how captured medical images are displayed will be described as a first example of control according to the display control method.

The control device 200 causes, for example, a first captured medical image and a second captured medical image to be displayed in different display areas of the display screen.

For example, the control device 200 causes the display such that the display area where the first captured medical image is displayed becomes larger than the display area where the second captured medical image is displayed. The control device 200 causes, for example, the first captured medical image to be displayed on the whole display screen, and the second captured medical image to be displayed on a part of the display screen. The control device 200 realizes "display of the first captured medical image on the whole display screen, and display of the second captured medical image on a part of the display screen" by the Picture-in-Picture (PIP) technique.

Furthermore, for example, the control device 200 may divide the display screen into plural areas, and cause the first captured medical image and the second captured medical image to be displayed respectively in these plural areas. The size of the display area where the first captured medical image is displayed may be the same as, or different from, the size of the display area where the second captured medical image is displayed.

How the captured medical images according to the embodiment are displayed is not limited to the above describe examples.

For example, the control device 200 may display the first captured medical image and the second captured medical image superimposed on the same display area of the display screen. If the first captured medical image and the second captured medical image are displayed superimposed on each other, for example, the control device 200 detects the same object from each of the first captured medical image and the second captured medical image, and alpha-blends the first captured medical image and second captured medical image such that positions of the detected object overlap each other.

Furthermore, if the medical observation system according to the embodiment has plural display devices, for example, the control device 200 may simultaneously display the first captured medical image and second captured medical image respectively on display screens of these different display devices. By transmitting, in synchronization, display control signals and image signals respectively to the display device caused to display thereon the first captured medical image and the display device caused to display thereon the second captured medical image, the display control signals and image signals corresponding respectively to these display devices, the first captured medical image and the second captured medical image are simultaneously displayed on the display screen of the different display devices respectively.

Furthermore, how the captured medical images according to the embodiment are displayed may be changeable. For example, the control device 200 changes how the captured medical images are displayed, based on manipulation of a manipulation device included in the control device 200 or a manipulation device external to the control device 200.

(2) Second Example of Control Related to Display Control Method: Control Related to Specification of Second Captured Medical Image Control related to specification of a second captured medical image will be described as a second example of the control related to the display control method.

As described above, the second captured medical image according to the embodiment is "a captured medical image captured in the second imaging mode before a first captured medical image". For example, the control device 200 extracts, from image data stored in the storage device 400, captured medical images captured in the second imaging mode, based on: a first captured medical image being displayed on the display screen (an example of a first captured medical image serving as a reference); or a first captured medical image to be displayed on the display screen (another example of the first captured medical image serving as the reference), the extracted captured medical images serving as candidates for the second captured medical image. The control device 200 determines a time point, at which the first captured medical image serving as the reference was captured, by, for example, referring to meta data of image data representing the first captured medical image serving as the reference. The control device 200 then specifies the second captured medical image from the extracted captured medical images serving as candidates for the second captured medical image.

If the number of captured medical images serving as candidates is one, the control device 200 specifies this captured medical image serving as a candidate as the second captured medical image.

Furthermore, if there are plural captured medical images serving as candidates, for example, the control device 200 specifies a captured medical image to be displayed simultaneously with the first captured medical image, from the plural captured medical images serving as candidates, as described, for example, in Sections (a) to (c) below. The control device 200 then causes the specified captured medical image to be displayed as the second captured medical image, simultaneously with the first captured medical image, on the display screen.

(a) First Method of Determining Second Captured Medical Image

The control device 200 specifies, as the second captured medical image, for example, a captured medical image captured in the second imaging mode within a predetermined time period from the time point, at which the first captured medical image serving as the reference was captured.

The predetermined time period may be a preset fixed time period (for example, 20 seconds, or one minute), or may be a variable time period that is variable based on manipulation by a person, such as a medical worker, who uses the medical observation system 1000. If the predetermined time period is a fixed time period, the predetermined time period is set at the time of designing or at the time of manufacturing, in consideration of, for example, imaging mode switching performance in the medical observation device 100 (this performance being determined based on, for example, a time period, in which a change of the imaging mode is completed in the medical observation device 100). Furthermore, if the predetermined time period is a variable time period, the predetermined time period is set by manipulation of, for example, a manipulation device included in the control device 200 or a manipulation device, such as a remote controller, which is external to the control device 200, by a user, such as a surgical operator or a nurse, who uses the control device 200 (an example of a device that functions as a medical display control device in the medical observation system 1000).

If there are plural captured medical images captured in the second imaging mode in the predetermined time period, for example, the control device 200 specifies, as the second captured medical image, a captured medical image randomly selected from the plural captured medical images. Furthermore, if there are plural captured medical images captured in the second imaging mode in the predetermined time period, for example, the control device 200 specifies the second captured medical image by combining another determination method, such as a later described determination method according to a second example.

(b) Second Method of Determining Second Captured Medical Image

The control device 200 specifies, as the second captured medical image, for example, an image that has been evaluated most highly, from captured medical images captured in the second imaging mode before the first captured medical image serving as a reference.

For example, the control device 200 estimates the amount of noise in each of the captured medical images serving as candidates, by using any method that enables estimation of noise from an image, such as Bayesian estimation where a noise quantity model is used. The control device 200 then specifies, as the second captured medical image, the captured medical image serving as the candidate with the least amount of noise.

The method of evaluating an image according to the embodiment is not limited to the above described example. For example, the control device 200 is able to perform any processing enabling quantitative evaluation of an image, and specify, as the second captured medical image, a captured medical image having the highest evaluation value.

Furthermore, as described in Section (a) above, by combination between the second determination method and the first determination method described in Section (a) above, the control device 200 is able to specify the second captured medical image.

(c) Third Method of Determining Second Captured Medical Image

The control device 200 specifies, as the second captured medical image, an image that has been selected based on a selecting manipulation for selecting an image, from captured medical images captured in the second imaging mode before the first captured medical image.

The control device 200 specifies the image selected based on the selecting manipulation, based on, for example, a signal corresponding to the selecting manipulation, the signal being acquired from a manipulation device included in the control device 200 or a manipulation device external to the control device 200. The control device 200 then specifies the specified image, as the second captured medical image.

If a third determination method is used, the control device 200 causes, for example, a UI to be automatically displayed on the display screen of the display device 300 or the like, the UI being for display of a list of captured medical images serving as candidates. Furthermore, when the third determination method is used, the control device 200 may cause, for example, a UI to be displayed based on a signal corresponding to a predetermined manipulation acquired from a manipulation device included in the control device 200, the UI being for display of a list of captured medical images serving as candidates.

If there are plural captured medical images serving as candidates, for example, the control device 200 specifies the second captured medical image as described in Sections (a) to (c) above. Needless to say, methods of determining the second captured medical image are not limited to the examples described in Sections (a) to (c) above.

(3) Third Example of Control Related to Display Control Method: Control Related to Start and End of Display for Simultaneous Display of First Captured Medical Image and Second Captured Medical Image Described as a third example of the control related to the display control method is control related to start and end of display for simultaneous display of a first captured medical image and a second captured medical image. Hereinafter, simultaneous display of a first captured medical image and a second captured medical image may be referred to as "simultaneous display".

The control device 200 performs, for example, the control described in Section (3-1) below or the control described in Section (3-2) below, as the control related to start and end of simultaneous display.

(3-1) First Example of Control Related to Start and End of Simultaneous Display

When an imaging device to be controlled, such as the imaging device 106 included in the medical observation device 100, is determined to be in the first imaging mode, the control device 200 causes a first captured medical image and a second captured medical image to be simultaneously displayed.

When a first mode switching manipulation for switching the second imaging mode to the first imaging mode is detected, the control device 200 determines that the imaging device is in the first imaging mode.

In an example where the imaging device to be controlled is the imaging device 106 included in the medical observation device 100, the control device 200 determines that the first mode switching manipulation has been detected, if, for example, a switching signal corresponding to the first imaging mode (an example of a switching signal according to manipulation of the imaging mode selecting switch 130) has been acquired from the medical observation device 100.

The method of detecting the first mode switching manipulation in the control device 200 is not limited to the above described example. For example, if the imaging mode in the imaging device 106 included in the medical observation device 100 is switched over by an external manipulation device, such as a remote controller, the control device 200 is able to detect the first mode switching manipulation, based on a signal acquired from the external manipulation device.

Furthermore, if the imaging device to be controlled is determined to be in the second imaging mode after the imaging device is determined to be in the first imaging mode, the control device 200 causes a captured medical image to be displayed, the captured medical image having been captured in the imaging device in the second imaging mode. This captured medical image captured in the second imaging mode is different from the second captured medical image, and is a captured medical image not dependent on the time point, at which the first captured medical image was captured.

If a second mode switching manipulation for switching the first imaging mode to the second imaging mode has been detected, the control device 200 determines that the imaging device is in the second imaging mode.

In an example where the imaging device to be controlled is the imaging device 106 included in the medical observation device 100, the control device 200 determines that the second mode switching manipulation has been detected, if, for example, a switching signal corresponding to the second imaging mode (another example of the switching signal according to the manipulation of the imaging mode selecting switch 130) has been acquired from the medical observation device 100.

The method of detecting the second mode switching manipulation in the control device 200 is not limited to the above described example. For example, if the imaging mode in the imaging device 106 included in the medical observation device 100 is switched over by an external manipulation device, the control device 200 is able to detect the second mode switching manipulation, based on a signal acquired from the external manipulation device.

(3-2) Second Example of Control Related to Start and End of Simultaneous Display The control device 200 causes the first captured medical image and the second captured medical image to be simultaneously displayed, if a display changing manipulation for changing display is detected when the first captured medical image is being displayed.

In an example where an imaging device to be controlled is the imaging device 106 included in the medical observation device 100, the control device 200 determines that the display changing manipulation has been detected, if, for example, a signal indicating that the state of the display changing switch 132 has changed is acquired from the medical observation device 100.

The method of detecting the display changing manipulation in the control device 200 is not limited to the above described example. For example, if the change of display is performed by manipulation of an external manipulation device, such as a remote controller, the control device 200 is able to detect the display changing manipulation based on a signal acquired from the external manipulation device.

Furthermore, the control device 200 causes only a first captured medical image to be displayed if a display changing manipulation is detected further after the first captured medical image and a second captured medical image are simultaneously displayed based on a display changing manipulation.

(4) Fourth Example of Control Related to Display Control Method: Control Related to Change of Second Captured Medical Image Control related to change of a second captured medical image will be described as a fourth example of the control related to the display control method.

If a selecting manipulation for selecting an image is detected when a first captured medical image and a second captured medical image are being simultaneously displayed, the control device 200 changes the second captured medical image being displayed on the display screen to a second captured medical image corresponding to the selecting manipulation.

The control device 200 specifies an image selected based on the selecting manipulation, based on, for example, a signal corresponding to the selecting manipulation, the signal being acquired from a manipulation device included in the control device 200 or a manipulation device external to the control device 200. The image specified as described above corresponds to the second captured medical image corresponding to the selecting manipulation. The control device 200 then replaces the second captured medical image being displayed on the display screen, with the specified image.

When the control related to the fourth example is performed, the control device 200 may cause, for example, a UI to be displayed based on a signal corresponding to a predetermined manipulation acquired from a manipulation device or the like included in the control device 200, the UI being for display of a list of second captured medical images serving as replacement candidates for the second captured medical image being displayed.

When the control related to the fourth example is performed, a medical worker, such as a surgical operator, is able to replace a second captured medical image displayed simultaneously with a first captured medical image, with a desired second captured medical image, and thus convenience for the medical worker is able to be improved.

(5) Another Example of Control Related to Display Control Method

Examples of the control related to the display control method according to the embodiment are not limited to the first example described in Section (1) above to the fourth example described in Section (4) above.

For example, the control device 200 may simultaneously display "a captured medical image captured in the second imaging mode" and "a captured medical image captured in the first imaging mode before the captured medical image captured in the second imaging mode".

Furthermore, the control device 200 may display one or more other images, together with a captured medical image. Examples of the other images include: an image related to a patient who receives medical intervention, such as an image depicting vitals of a patient who receives medical intervention; an image depicting a flow of a surgical operation (for example, an image indicating content of a surgical operation manual according to operative surgical procedures); and a UI image.

[III] Example of Operation Realized by Processing Related to Display Control Method According to Embodiment Described next is an example of operation of the medical observation system according to the embodiment, the operation being realized by the processing related to the display control method according to the embodiment.

Figure 6:
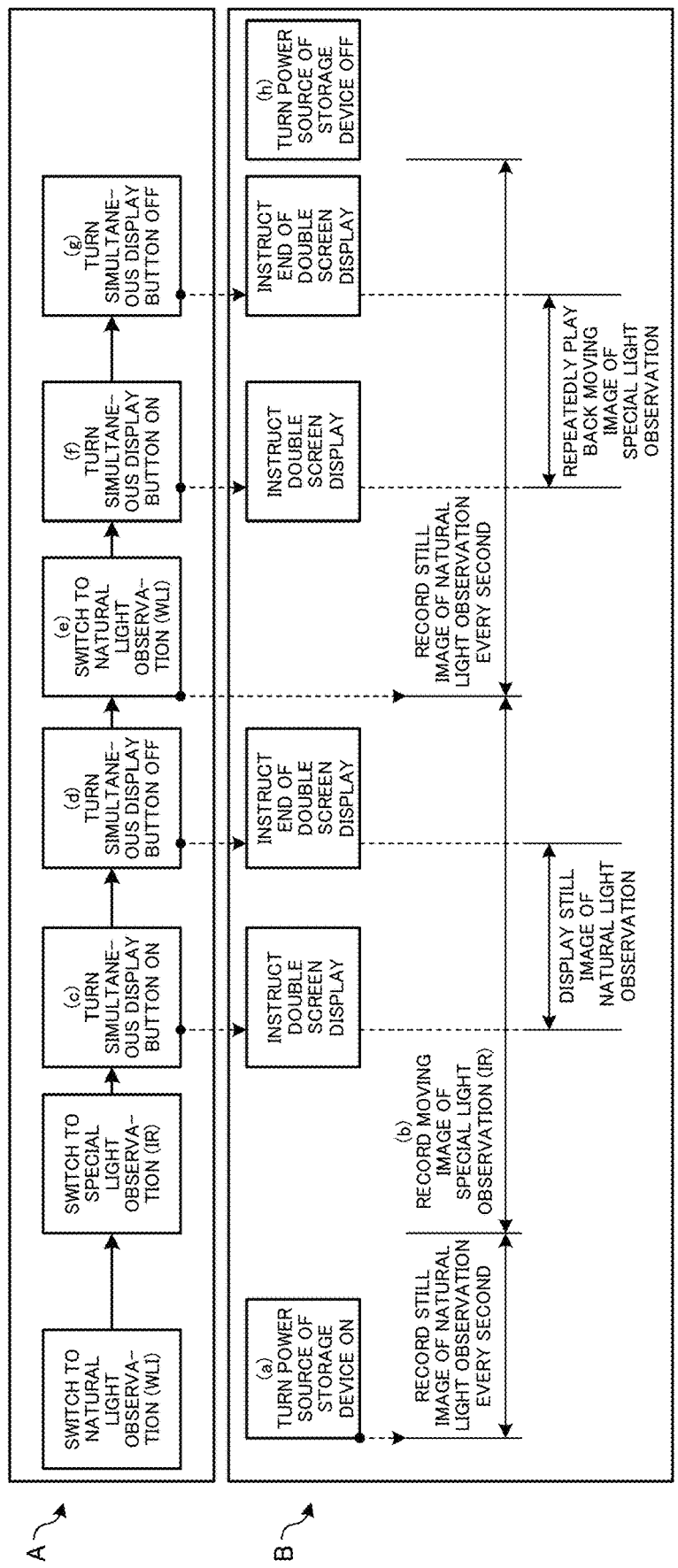
FIG. 6 is an explanatory diagram for explanation of an example of operation of the medical observation system according to the embodiment, the operation being realized by processing related to the display control method according to the embodiment.

FIG. 6 is an explanatory diagram for explanation of an example of operation of the medical observation system 1000 according to the embodiment, the operation being realized by the processing related to the display control method according to the embodiment. In FIG. 6, "A" represents an example of state transition of the medical observation device 100, the state transition corresponding to manipulation of various manipulation devices included in the medical observation device 100. Furthermore, in FIG. 6, "B" represents an example of operation of the control device 200 and the storage device 400.

Furthermore, FIG. 7 to FIG. 10 are diagrams illustrating examples of captured medical images displayed on the display screen of the display device 300 by the operation of the medical observation system 1000 illustrated in FIG. 6.

Figure 7:
FIG. 7 is a diagram illustrating an example of a captured medical image displayed on a display screen of a display device, through the operation of the medical observation system illustrated in FIG. 6.

FIG. 7 illustrates an example where a captured medical image, which is acquired when the medical observation device 100 is involved in natural light observation, is being displayed on the display screen.

Figure 8:
FIG. 8 is a diagram illustrating an example of a captured medical image displayed on the display screen of the display device, through the operation of the medical observation system illustrated in FIG. 6.

FIG. 8 illustrates an example where a first captured medical image, which is acquired when the medical observation device 100 is involved in special light observation, is being displayed on the display screen. FIG. 8 illustrates, as the first captured medical image, an example of a captured image resulting from imaging with light of a near infra-red wavelength band.

Figure 9:
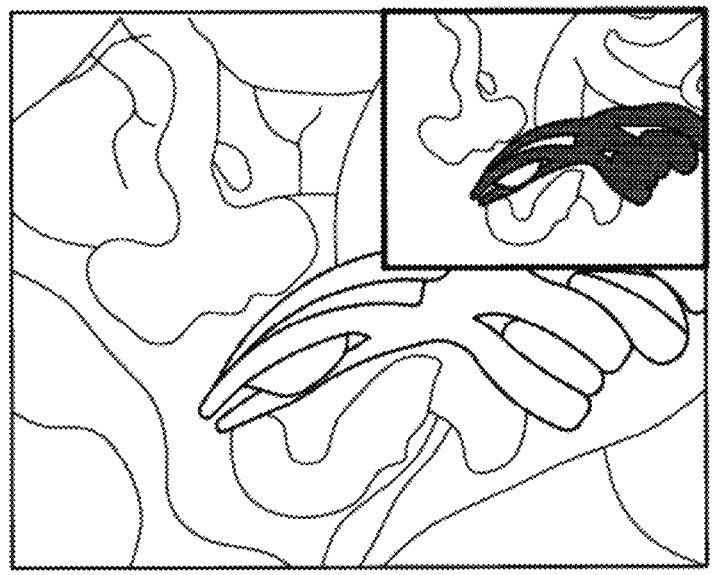
FIG. 9 is a diagram illustrating an example of captured medical images displayed on the display screen of the display device, through the operation of the medical observation system illustrated in FIG. 6.

FIG. 9 illustrates "an example where a first captured medical image and a second captured medical image are being simultaneously displayed on the display screen. FIG. 9 illustrates, as the first captured medical image, an example of a captured image resulting from imaging with light of a near infra-red wavelength band, similarly to FIG. 8. Furthermore, FIG. 9 illustrates, as the second captured medical image, an example of a captured medical image acquired when the medical observation device 100 is involved in natural light observation, similarly to FIG. 7.

Figure 10:
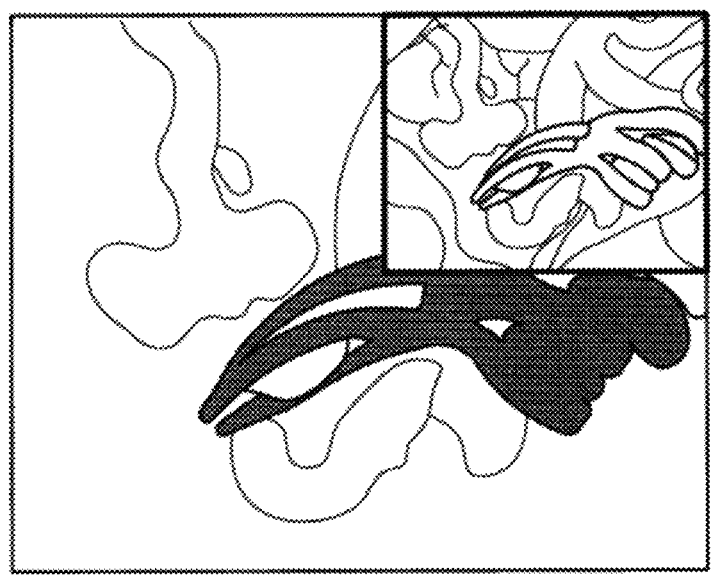
FIG. 10 is a diagram illustrating an example of captured medical images displayed on the display screen of the display device, through the operation of the medical observation system illustrated in FIG. 6.

FIG. 10 illustrates an example where "a captured medical image captured in the second imaging mode" and "a captured medical image captured in the first imaging mode before the captured medical image captured in the second imaging mode" are being simultaneously displayed on the display screen. FIG. 10 illustrates, as the second captured medical image, an example of a captured medical image acquired when the medical observation device 100 is involved in natural light observation, similarly to FIG. 7. Furthermore, FIG. 10 illustrates, as the first captured medical image, an example of a captured image resulting from imaging with light of a near infra-red wavelength band, similarly to FIG. 8.

An example of the operation of the medical observation system 1000, the operation being realized by the processing related to the display control method according to the embodiment, will be described below by reference, as appropriate, to FIG. 6 to FIG. 10.

(i) (a) in FIG. 6

As the power source of the storage device 400 is turned into an on-state when the medical observation device 100 is involved in natural light observation, a still image (an example of the second captured medical image) of the natural light observation is recorded every second (an example of the predetermined time interval). Furthermore, a captured medical image, which is, for example, illustrated in FIG. 7 and acquired when natural light observation is performed, is displayed on the display screen of the display device 300.

(ii) (b) in FIG. 6

For example, when a surgical operator manipulates the imaging mode selecting switch 130 of the medical observation device 100, such that the imaging mode selecting switch 130 is brought into a state where "IR" illustrated in FIG. 4 has been selected, a moving image of special light observation (an example of the first captured medical image) is recorded into the storage device 400. Furthermore, the first captured medical image illustrated in FIG. 8, for example, is displayed on the display screen of the display device 300.

(iii) (c) in FIG. 6

If a surgical operator performs manipulation for bringing the display changing switch 132 of the medical observation device 100 into the on-state when the medical observation device 100 is involved in special light observation, for example, the first captured medical image and the second captured medical image are simultaneously displayed on the display screen of the display device 300, for example, as illustrated in FIG. 9.

The first captured medical image displayed is a first captured medical image that is a result of the current imaging in the first imaging mode. Furthermore, the second captured medical image simultaneously displayed with the first captured medical image is a captured medical image captured in the second imaging mode before the first captured medical image. The second captured medical image displayed simultaneously with the first captured medical image may be, for example, the still image recorded in the storage device 400 at (a) in FIG. 6. The second captured medical image simultaneously displayed with the first captured medical image may be changeable by manipulation of any manipulation device, such as a remote controller.

(iv) (d) in FIG. 6

When a surgical operator performs manipulation for turning the display changing switch 132 of the medical observation device 100 into the off-state further, for example, the first captured medical image, which is a captured medical image corresponding to the current imaging mode of the medical observation device 100, is displayed on the display screen of the display device 300.

(v) (e) in FIG. 6

For example, when a surgical operator manipulates the imaging mode selecting switch 130 of the medical observation device 100, such that the imaging mode selecting switch 130 is brought into a state where "WLI" illustrated in FIG. 4 has been selected, the medical observation device 100 is switched over from special light observation to natural light observation. When the imaging mode is changed in the medical observation device 100; in the storage device 400, recording of the moving image of special light observation (an example of the first captured medical image) is stopped and a still image of natural light observation (an example of the second captured medical image) is recorded every second (an example of the predetermined time interval).

(vi) (f) in FIG. 6

When a surgical operator performs manipulation for turning the display changing switch 132 of the medical observation device 100 into the on-state when the medical observation device 100 is involved in special light observation, for example, a "captured medical image captured in the second imaging mode" and a "captured medical image captured in the first imaging mode before the captured medical image captured in the second imaging mode" are simultaneously displayed on the display screen of the display device 300, for example, as illustrated in FIG. 10.

The "captured medical image captured in the second imaging mode" displayed is a captured medical image that is a result of the current imaging in the second imaging mode. Furthermore, the "captured medical image captured in the first imaging mode before the captured medical image captured in the second imaging mode" may be, for example, the moving image recorded in the storage device 400 at (b) in FIG. 6. For example, if a moving image, such as the moving image recorded in the storage device 400 at (b) in FIG. 6, is displayed on the display screen, for example, the moving image is repeatedly played back. The "captured medical image captured in the first imaging mode before the captured medical image captured in the second imaging mode" may be changeable by manipulation of any manipulation device, such as a remote controller.

(vii) (g) in FIG. 6

When a surgical operator performs manipulation for turning the display changing switch 132 of the medical observation device 100 into the off-state further, for example, a captured medical image, which is a captured medical image corresponding to the current imaging mode of the medical observation device 100 and which is acquired when natural light observation is performed, is displayed on the display screen of the display device 300.

(viii) (h) in FIG. 6

When the power source of the storage device 400 is turned into the off-state, recording of the still image (an example of the second captured medical image) of natural light observation is stopped.

The operation of the medical observation system 1000 described by reference to FIG. 6 is realized, for example, by the processing being performed in the control device 200, the processing being related to the display control method according to the embodiment.

Examples of the operation of the medical observation system 1000 realized by the processing related to the display control method according to the embodiment are not limited to the example described by reference to FIG. 6. For example, the example described by reference to FIG. 6 is an example where two captured medical images are simultaneously displayed on the display screen, but three or more captured medical images may be simultaneously displayed on the display screen. Furthermore, as described above, one or more other images may be displayed together with a captured medical image.

[IV] Example of Effects Achieved by Use of Display Control Method According to Embodiment Use of the display control method according to the embodiment achieves, for example, the following effects in the medical observation system according to the embodiment. Needless to say, effects achieved by use of the display control method according to the embodiment are not limited to the following examples.

- Since a captured medical image (a still image or a moving image) acquired in the immediately preceding imaging mode is displayed simultaneously with a captured medical image acquired in the current imaging mode, the imaging device does not need to have a configuration including two CCDs like a surgical microscope where the technique described in Patent Literature 1 is used. Therefore, the cost of the imaging device is able to be prevented from increasing, and downsizing of the imaging device is facilitated.
- When time-series imaging is performed in an imaging device, the frame rate may be decreased, but in the medical observation system according to the embodiment, since captured medical images are recorded per imaging mode, the frame rate is not decreased.
- Simultaneous display of a captured medical image of special light observation (the first captured medical image) and a captured medical image of natural light observation (an example of the second captured medical image) on the display screen enables facilitation of observation of a part that is difficult to be identified when only the captured medical image of special light observation is displayed.
- As illustrated in FIG. 9, for example, by display of a captured medical image of special light observation (the first captured medical image) and a captured medical image of natural light observation (an example of the second captured medical image) in different display areas of the display screen, a medical worker, such as a surgical operator, is able to distinguish a fine blood vessel more easily.

Program According to Embodiment

By a program (for example, a program that is able to execute the processing related to the display control method according to the embodiment) being executed by a processor or the like in a computer system, the program being for causing the computer system to function as the medical display control device according to the embodiment, captured medical images captured in different imaging modes in a single imaging device are able to be simultaneously displayed on a display screen. The computer system according to the embodiment may be a single computer, or plural computers. The sequential processing related to the display control method according to the embodiment is executed by the computer system according to the embodiment.

Furthermore, the above described effects achieved by the display realized by the processing related to the display control method according to the embodiment are able to be achieved by execution of the program by the processor or the like in the computer system, the program being for causing the computer system to function as the medical display control device according to the embodiment.

Preferred embodiments of the present disclosure have been described thus far in detail by reference to the appended drawings, but the technical scope of the present disclosure is not limited to these examples. It is evident that any person having ordinary knowledge in the technical field of the present disclosure is able to devise various modified examples and reformed examples within the scope of technical ideas described in the claims, and these examples will of course be understood as belonging to the technical scope of the present disclosure.

For example, according to the above description, the program (a computer program) for causing the computer system to function as the medical display control device according to the embodiment is provided, but according to the embodiment, a recording medium having, stored therein, the program may also be provided further.

The above described configurations are examples of the embodiment, and of course belong to the technical scope of the present disclosure.

Furthermore, the effects described in this specification are just explanatory or exemplary, and are not limiting. That is, the techniques according to the present disclosure may achieve, together with the above described effects, or instead of the above described effects, any other effect evident to those skilled in the art from the description in this specification.

The following configurations also belong to the technical scope of the present disclosure.

(1)

A medical display control device, comprising:

a display control unit that causes a first captured medical image and a second captured medical image to be simultaneously displayed, the first captured medical image having been captured in an imaging device in a first imaging mode where imaging is performed with special light, the second captured medical image having been captured in the imaging device in a second imaging mode different from the first imaging mode before the first captured medical image.

(2)

The medical display control device according to (1), wherein the display control unit causes the first captured medical image and the second captured medical image to be displayed in different display areas of a display screen.

(3)

The medical display control device according to (2), wherein the display control unit causes the display such that the display area where the first captured medical image is displayed is larger than the display area where the second captured medical image is displayed.

(4)

The medical display control device according to (3), wherein the display control unit causes the first captured medical image to be displayed on the whole display screen, and the second captured medical image to be displayed on a part of the display screen.

(5)

The medical display control device according to (1), wherein the display control unit causes the first captured medical image and the second captured medical image to be displayed superimposed on the same display area of a display screen.

(6)

The medical display control device according to (1), wherein the display control unit causes the first captured medical image and the second captured medical image to be displayed respectively on display screens of different display devices.

(7)

The medical display control device according to any one of (1) to (6), wherein the display control unit causes the first captured medical image and the second captured medical image to be simultaneously displayed when the imaging device is determined to be in the first imaging mode.

(8)

The medical display control device according to (7), wherein the display control unit determines that the imaging device is in the first imaging mode when a first mode switching manipulation for switching the second imaging mode to the first imaging mode is detected.

(9)

The medical display control device according to (7) or (8), wherein the display control unit causes a captured medical image to be displayed, the captured medical image having been captured in the imaging device in the second imaging mode, when the imaging device is determined to be in the second imaging mode after the imaging device is determined to be in the first imaging mode.

(10)

The medical display control device according to (9), wherein the display control unit determines that the imaging device is in the second imaging mode when a second mode switching manipulation for switching the first imaging mode to the second imaging mode is detected.

(11)

The medical display control device according to any one of (1) to (6), wherein the display control unit causes the first captured medical image and the second captured medical image to be simultaneously displayed when a display changing manipulation for changing display is detected when the first captured medical image is being displayed.

(12)

The medical display control device according to (11), wherein the display control unit causes only the first captured medical image to be displayed when the display changing manipulation is detected further after the first captured medical image and the second captured medical image are simultaneously displayed based on the display changing manipulation.

(13)

The medical display control device according to any one of (1) to (12), wherein if a selecting manipulation for selecting an image is detected when the first captured medical image and the second captured medical image are being simultaneously displayed, the display control unit changes the second captured medical image being displayed on a/the display screen to the second captured medical image corresponding to the selecting manipulation.

(14)

The medical display control device according to any one of (1) to (13), wherein the second captured medical image is a captured medical image captured in the second imaging mode within a predetermined time period from a time point, at which the first captured medical image was captured.

(15)

The medical display control device according to (14), wherein the predetermined time period is a fixed time period that has been set beforehand, or a time period set based on manipulation by a user who uses the medical display control device.

(16)

The medical display control device according to any one of (1) to (15), wherein the second captured medical image is an image that has been evaluated most highly, the image being from captured medical images captured in the second imaging mode before the first captured medical image.

(17)

The medical display control device according to any one of (1) to (13), wherein the second captured medical image is an image selected based on a selecting manipulation for selecting the image, the image being from captured medical images captured in the second imaging mode before the first captured medical image.

(18)

A medical observation device, comprising:
an arm formed of plural links connected to one another via joints;
an imaging device supported by the arm; and
a display control unit that causes a first captured medical image and a second captured medical image to be simultaneously displayed, the first captured medical image having been captured in the imaging device in a first imaging mode where imaging is performed with special light, the second captured medical image having been captured in the imaging device in a second imaging mode different from the first imaging mode before the first captured medical image.

(19)

A display control method executed by a medical display control device, the display control method including:
a step of simultaneously displaying a first captured medical image captured in an imaging device in a first imaging mode where imaging is performed with special light, and a second captured medical image captured in the imaging device in a second imaging mode different from the first imaging mode before the first captured medical image.

(20)

A medical observation system, comprising:
a medical observation device including: an arm formed of plural links connected to one another via joints; and an imaging device supported by the arm;
a display device; and
a medical display control device including a display control unit that causes a first captured medical image and a second captured medical image to be simultaneously displayed on a display screen of the display device, the first captured medical image having been captured in the imaging device in a first imaging mode where imaging is performed with special light, the second captured medical image having been captured in the imaging device in a second imaging mode different from the first imaging mode before the first captured medical image.

REFERENCE SIGNS LIST

100 MEDICAL OBSERVATION DEVICE
102 BASE
104 ARM
106 IMAGING DEVICE
110a, 110b, 110c, 110d, 110e, 110f JOINT
112a, 112b, 112c, 112d, 112e, 112f LINK
120 IMAGING MEMBER
122 CYLINDRICAL MEMBER
124 ZOOM SWITCH
126 FOCUS SWITCH
128 OPERATION MODE SELECTING SWITCH
130 IMAGING MODE SELECTING SWITCH
132 DISPLAY CHANGING SWITCH
200 CONTROL DEVICE
300 DISPLAY DEVICE
400 STORAGE DEVICE
1000 MEDICAL OBSERVATION SYSTEM
OP SURGICAL OPERATOR
PA PATIENT
FS FOOT SWITCH

The invention claimed is:

1. A medical system, comprising:
a medical display controller operably coupled to an electronic display and a medical imaging device, wherein the medical display controller includes processing circuitry configured to:
control the imaging device to capture medical images with a first light;
control the imaging device to capture medical images with a second light different from the first light;
cause a first medical image having been captured with the first light and a second medical image having been captured with the second light different from the first light to be simultaneously displayed on the electronic display in a simultaneous display mode in a case where a first display changing manipulation for changing display is detected; and
cause only one of the first medical image or the second medical image to be displayed on the electronic display in a case where a second display changing manipulation for changing display is detected while the first medical image and the second medical image are simultaneously displayed based on the first display changing manipulation, wherein
in a case where the first display changing manipulation for changing display is detected while the processing circuitry is controlling the electronic display to display images captured with the first light, the simultaneous display mode is a first mode where the first medical image is an image having been captured as a result of a current imaging and the second medical image is an image having been captured before the first medical image, and
in a case where the first display changing manipulation for changing display is detected while the processing circuitry is controlling the electronic display to display images captured with the second light, the simultaneous display mode is a second mode where the second medical image is an image having been captured as a result of a current imaging and the first medical image is a moving image having been captured before the second medical image, the first medical image being repeatedly played back.

2. The medical display control device according to claim 1, wherein the first light is special light different from natural light.

3. The medical display control device according to claim 2, wherein the special light is light with a specific wavelength band limited by a filter.

4. The medical display control device according to claim 1, wherein the first light is near infra-red wavelength band light or fluorescent wavelength band light.

5. The medical display control device according to claim 4, wherein the wavelength of the fluorescent wavelength band light is the wavelength corresponding to fluorescent observation by use of 5-aminolevulinic acid.

6. The medical display control device according to claim 1, wherein the first mode includes one or more modes.

7. The medical display control device according to claim 1, wherein the second light is natural light or narrow band light.

8. The medical display control device according to claim 1, wherein the second mode includes one or more modes.

9. The medical display control device according to claim 1, wherein the medical imaging device is an endoscope or a microscope.

10. The medical display control device according to claim 1, wherein the processing circuitry is configured to cause the first medical image and the second medical image to be displayed in different display areas of a display screen.

11. The medical display control device according to claim 10, wherein the processing circuitry is configured to cause the electronic display such that the display area where the first medical image is displayed is larger than the display area where the second medical image is displayed.

12. The medical display control device according to claim 11, wherein the processing circuitry is configured to cause the first medical image to be displayed on the whole display screen and the second medical image to be displayed on a part of the display screen.

13. The medical display control device according to claim 1, wherein the processing circuitry is configured to cause the first medical image and the second medical image to be displayed superimposed on the same display area of a display screen.

14. The medical display control device according to claim 1, wherein the processing circuitry is configured to cause the first captured medical image and the second captured medical image to be displayed respectively on display screens of different display devices.

15. A medical display control method performed by a medical display controller operably coupled to an electronic display and a medical imaging device, the method comprising:

controlling, using processing circuitry of the medical display controller the imaging device to capture medical images with a first light:

controlling, using the processing circuitry of the medical display controller, the imaging device to capture medical images with a second light different from the first light;

causing, using the processing circuitry of the medical display controller, a first medical image having been captured with the first light and a second medical image having been captured with the second light different from the first light to be simultaneously displayed on the electronic display in a simultaneous display mode in a case where a first display changing manipulation for changing display is detected; and causing, using the processing circuitry of the medical display controller, only one of the first medical image or the second medical image to be displayed on the electronic display in a case where a second display changing manipulation for changing display is detected while the first medical image and the second medical image are simultaneously displayed based on the first display changing manipulation, wherein in a case where the first display changing manipulation for changing display is detected while the processing circuitry is controlling the electronic display to display images captured with the first light, the simultaneous display mode is a first mode where the first medical image is an image having been captured as a result of a current imaging and the second medical image is an image having been captured before the first medical image, and in a case where the first display changing manipulation for changing display is detected while the processing circuitry is controlling the electronic display to display images captured with the second light, the simultaneous display mode is a second mode where the second medical image is an image having been captured as a result of a current imaging and the first medical image is a moving image having been captured before the second medical image, the first medical image being repeatedly played back.

16. The medical display control method according to claim 13, wherein the special light is light with a specific wavelength band limited by a filter.

17. The medical display control method according to claim 15, wherein the first light is near infra-red wavelength band light or fluorescent wavelength band light.

18. The medical display control method according to claim 17, wherein the wavelength of the fluorescent wavelength band light is the wavelength corresponding to fluorescent observation by use of 5-aminolevulinic acid.

19. The medical display control method according to claim 15, wherein the second light is natural light or narrow band light.

* * * * *